United States Patent [19]

McDonough et al.

[11] Patent Number: 5,766,849

[45] Date of Patent: *Jun. 16, 1998

[54] METHODS OF AMPLIFYING NUCLEIC ACIDS USING PROMOTER-CONTAINING PRIMER SEQUENCE

[75] Inventors: Sherrol H. McDonough; Daniel L. Kacian; Nanibhushan Dattagupta; Diane L. McAllister; Philip W. Hammond, all of San Diego; Thomas B. Ryder, Escondido, all of Calif.

[73] Assignee: Gen-Probe Incorporated, San Diego, Calif.

[*] Notice: The term of this patent shall not extend beyond the expiration date of Pat. No. 5,554,516.

[21] Appl. No.: 345,861

[22] Filed: Nov. 28, 1994

Related U.S. Application Data

[63] Continuation of Ser. No. 925,405, Aug. 4, 1992, abandoned, and a continuation-in-part of Ser. No. 550,837, Jul. 10, 1990, Pat. No. 5,480,784, and a continuation-in-part of Ser. No. 379,501, Jul. 11, 1989, abandoned, said Ser. No. 925,405, is a continuation-in-part of Ser. No. 855,732, Mar. 19, 1992, Pat. No. 5,399,491.

[51] Int. Cl.⁶ .................... C07H 21/02; C07H 21/04; C12P 19/34; C12Q 1/68
[52] U.S. Cl. .................... 435/6; 435/91.2; 435/91.21; 536/23.1; 536/24.33; 935/77; 935/78
[58] Field of Search .................. 435/6, 91.2, 91.21; 935/77, 78; 536/23.1, 24.33

[56] References Cited

U.S. PATENT DOCUMENTS

| 4,683,202 | 7/1987 | Mullis | 435/91 |
|---|---|---|---|
| 5,399,491 | 3/1995 | Kacian et al. | 435/91.21 |

FOREIGN PATENT DOCUMENTS

| 559709 | 2/1988 | Canada. |
| 0329822 | 8/1988 | European Pat. Off.. |
| 0373960 | 12/1989 | European Pat. Off.. |
| 0398677 | 11/1990 | European Pat. Off.. |
| 0408295 | 1/1991 | European Pat. Off.. |
| 0439182 | 1/1991 | European Pat. Off.. |
| 0461045 | 12/1991 | European Pat. Off.. |
| 0587266 | 5/1993 | European Pat. Off.. |
| 2651505 | 3/1991 | France. |
| 2659086 | 9/1991 | France. |
| 8706270 | 10/1987 | WIPO. |
| 8803957 | 6/1988 | WIPO. |
| 8810315 | 12/1988 | WIPO. |
| 8901050 | 2/1989 | WIPO. |
| 29014439 | 11/1990 | WIPO. |
| 9101384 | 2/1991 | WIPO. |
| 9115601 | 10/1991 | WIPO. |
| 9207957 | 5/1992 | WIPO. |
| 9222663 | 12/1992 | WIPO. |
| 9304201 | 3/1993 | WIPO. |

OTHER PUBLICATIONS

Grachev et al. Nuc. Acids Reg. 12(22) 8509–8524, 1989.
Golomb et al. J. Biol. Chem. 254(5) 1606–1613, 1979.
Leis et al. J. Virol. 45(2) 727–739, 1983.
Day, R. "How to Write and Publish a Scientific Paper", 2ⁿᵈ ed. ISI Press, 1983, p. 170.

(List continued on next page.)

Primary Examiner—W. Gary Jones
Assistant Examiner—Paul B. Tran
Attorney, Agent, or Firm—Lyon & Lyon LLP

[57] ABSTRACT

A method, composition and kit for synthesizing multiple copies of a target nucleic acid sequence autocatalytically under conditions of substantially constant temperature, ionic strength, and pH are provided in which multiple RNA copies of the target sequence autocatalytically generate additional copies using a mixture of blocked and unblocked primers and/or promoter-primers to initiate DNA and RNA synthesis, preferably with reduced non-specific product formation. The invention is useful for generating copies of a nucleic acid target sequence for purposes that include assays to quantitate specific nucleic acid sequences in clinical, environmental, forensic and similar samples, cloning and generating probes.

53 Claims, 1 Drawing Sheet

3' alkane diol modified nucleotide. When N = 3, the modification is referred to as RP.

OTHER PUBLICATIONS

Wilk et al., "Backbone-modified oligonucleotides containing a butaneodiol-1,3 moiety as a 'vicarious segment' for the deoxyribosyl moiety—synthesis and enzyme studies," *Nucleic Acids Research* 18:2065–2068 (1990).

Joyce, "Amplification, mutation and selection of catalytic RNA", Gene, 82:83–87, 1989.

Lowary et al., "A Better Way to Make RNA for Physical Studies", Knippenberg, eds., Structure & Dynamics of RNA, Nato ASI Series, vol. 110, New York, Plenum Press (1986).

Murakawa et al., Direct Detection of HIV-1 RNA from AIDS and ARC Patient Samples, DNA, 7:287–295, 1988.

Mullis et al., "Specific Synthesis of DNA in Vitro via a Polymerase-Catalyzed Chain REaction", Methods in Enzymology, 155:335, 1987.

Watson et al., "Molecular Structure of Nucleic Acids", Nature, Apr. 25, 1953, p. 737.

Khorana, "Total Synthesis of a Gene", Science 203:614, 1979.

Okayama et al., "High-Efficiency Cloning of Full-Length cDNA", Molecular and Cellular Biology, 2:161–170, 1982.

Watson et al., "Genetical Implications of the Structure of Deoxyribonucleic Acid", Nature, 171:964, 1953.

Stent, "Molecular Biology of Bacterial Viruses", W. H. Freeman and Company, 1963.

Hayes, "The Genetics of Bacteria and their Viruses", John Wiley & Sons Inc., New York, Blackwell Scientific Publications 1964, 1968.

Lomonossoff et al., "The location of the first AUG codons in cowpea mosaic virus RNAs", Nucleic Acids Research, 10:4861, 1982.

Cashdollar et al., "Cloning the double-stranded RNA genes of reovirus: Sequence of the cloned S2 gene", Proc. Natl. Acad. Sci. USA, vol. 79, pp. 7644–7648, 1982.

Both et al., "A general strategy for cloning double-stranded RNA: nucleotide sequence of the Simian–11 rotavirus gene 8", Nucleic Acids Research, 10:7075, 1982.

Kupper et al., "Promoter dependent transcription of tRNA$_f$ Tyr genes using DNA fragments produced by restriction enzymes", Proc. Natl. Acad. Sci., USA, 72:4754, 1975.

Rossi et al., "An Alternate Method for Synthesis of Double-stranded DNA segments", J. Biological Chemistry 257:9226, 1982.

Zoller et al., "Oligonucleotide-Directed Mutagenesis of DNA Fragments Cloned into M13 Vectors", Methods in Enzymology, 100:468, 1983.

Guatelli et al., "Isothermal, in vitro amplification of nucleic acids by a multienzyme reaction modeled after retroviral replication", Proc. Natl. Acad. Sci., USA, 87:1874, 1990.

European search report for Appln. No. 90307503.4 dated Jul. 12, 1991.

Kwoh et al., Proc. Natl. Acad. Sci USA 86:1175, 1989.

Krug and Berger, Proc. Natl. Acad. Sci USA 86:3539, 1989.

Oyama et al., Journal of Biological Chemistry, 264:18808, 1989.

Grachev et al., Nuc. Acids Res. 12 (22) 1984, p. 8501.

Milligan et al., Nuc. Acids Res. 15(21) 1987, p. 8783.

Gubler, Guide to Molecular Cloning Techniques; Academic Press, NY NY, 1987, p. 330.

Krug et al., Guide to Molecular Cloning Techniques; Academic Press, NY NY, (1987) pp. 316–325.

Bethesda Research Laboratories Catalogue & Reference Guide, (1988) Bethesda Research Laboratories, Bethesda MD, p. 37.

Cox et al., J. Med. Microbiol., vol. 35 (1991), pp. 284–290.

J.S. Tyagi et al., Trop. Med. Parasitol. 41 (1990), pp. 294–296.

3' alkane diol modified nucleotide. When
N = 3, the modification is referred to as RP.

METHODS OF AMPLIFYING NUCLEIC ACIDS USING PROMOTER-CONTAINING PRIMER SEQUENCE

This is a continuation of application U.S. Ser. No. 07/925,405, filed Aug. 4, 1992, now abandoned, which is a continuation-in-part of application U.S. Ser. No. 07/855,732, filed Mar. 19, 1992, now U.S. Pat. No. 5,399,491, and a continuation-in-part of application U.S. Ser. No. 07/550,837, filed Jul. 10, 1990, now U.S. Pat. No. 5,480,784, and a continuation-in-part of application U.S. Ser. No. 07/379,501, filed Jul. 11, 1989, now abandoned.

FIELD OF THE INVENTION

This invention relates to methods for increasing the number of copies of a specific nucleic acid sequence or "target sequence" which may be present either alone or as a component, large or small, of a homogeneous or heterogeneous mixture of nucleic acids. The mixture of nucleic acids may be that found in a sample taken for diagnostic testing, environmental testing, for research studies, for the preparation of reagents or materials, for other processes such as cloning, or for other purposes.

The selective amplification of specific nucleic acid sequences is of value in increasing the sensitivity of diagnostic and environmental assays while maintaining specificity; increasing the sensitivity, convenience, accuracy and reliability of a variety of research procedures; and providing ample supplies of specific oligonucleotides for various purposes.

The present invention is particularly suitable for use in environmental and diagnostic testing due to the convenience with which it may be practiced.

BACKGROUND OF THE INVENTION

The detection and/or quantitation of specific nucleic acid sequences is an increasingly important technique for identifying and classifying microorganisms, diagnosing infectious diseases, detecting and characterizing genetic abnormalities, identifying genetic changes associated with cancer, studying genetic susceptibility to disease, and measuring response to various types of treatment. Such procedures have also found expanding uses in detecting and quantitating microorganisms in foodstuffs, environmental samples, seed stocks, and other types of material where the presence of specific microorganisms may need to be monitored. Other applications are found in the forensic sciences, anthropology, archaeology, and biology where measurement of the relatedness of nucleic acid sequences has been used to identify criminal suspects, resolve paternity disputes, construct genealogical and phylogenetic trees, and aid in classifying a variety of life forms.

A common method for detecting and quantitating specific nucleic acid sequences is nucleic acid hybridization. This method is based on the ability of two nucleic acid strands that contain complementary or essentially complementary sequences to specifically associate, under appropriate conditions, to form a double-stranded structure. To detect and/or quantitate a specific nucleic acid sequence (known as the "target sequence"), a labelled oligonucleotide (known as a "probe") is prepared that contains sequences complementary to those of the target sequence. The probe is mixed with a sample suspected of containing the target sequence, and conditions suitable for hybrid formation are created. The probe hybridizes to the target sequence if it is present in the sample. The probe-target hybrids are then separated from the single-stranded probe in one of a variety of ways. The amount of label associated with the hybrids is then measured as an indication of the amount of target sequence in the sample.

The sensitivity of nucleic acid hybridization assays is limited primarily by the specific activity of the probe, the rate and extent of the hybridization reaction, the performance of the method for separating hybridized and unhybridized probe, and the sensitivity with which the label can be detected. The most sensitive procedures may lack many of the features required for routine clinical and environmental testing such as speed, convenience, and economy. Furthermore, their sensitivities may not be sufficient for many desired applications.

As a result of the interactions among the various components and component steps of this type of assay, there is almost always an inverse relationship between sensitivity and specificity. Thus, steps taken to increase the sensitivity of the assay (such as increasing the specific activity of the probe) may result in a higher percentage of false positive test results. The linkage between sensitivity and specificity has been a significant barrier to improving the sensitivity of hybridization assays. One solution to this problem would be to specifically increase the amount of target sequence present using an amplification procedure. Amplification of a unique portion of the target sequence without amplification of a significant portion of the information encoded in the remaining sequences of the sample could give an increase in sensitivity while at the same time not compromising specificity.

A method for specifically amplifying nucleic acid sequences termed the "polymerase chain reaction" or "PCR" has been described by Mullis et al. (See U.S. Pat. Nos. 4,683,195, 4,683,202 and 4,800,159 and European patent applications 86302298.4, 86302299.2, and 87300203.4 and *Methods in Enzymology*, Volume 155, 1987, pp. 335–350.) The procedure uses repeated cycles of primer dependent nucleic acid synthesis occurring simultaneously using each strand of a complementary sequence as a template. The sequence that is amplified is defined by the locations of the primer molecules that initiate synthesis. The primers are complementary to the 3'-end portion of the target sequence or its complement and must complex with those sites in order for nucleic acid synthesis to begin. After extension product synthesis, the strands are separated, generally by thermal denaturation, before the next synthesis step. In the PCR procedure, copies of both strands of a complementary sequence are synthesized.

The strand separation step used in PCR to separate the newly synthesized strands at the conclusion of each cycle of the PCR reaction is often thermal denaturation. As a result, either a thermostable enzyme is required or new enzyme must be added between thermal denaturation steps and the initiation of the next cycle of DNA synthesis. The requirement of repeated cycling of reaction temperature between several different and extreme temperatures is a disadvantage of the PCR procedure. In order to make the PCR convenient, programmable thermal cycling instruments are required.

The PCR procedure has been coupled to RNA transcription by incorporating a promoter sequence into one of the primers used in the PCR reaction and then, after amplification by the PCR procedure for several cycles, using the double-stranded DNA as template for the transcription of single-stranded RNA. (See, e.g., Murakawa et al., *DNA* 7:287–295 (1988).)

Other methods for amplification of a specific nucleic acid sequence comprise a series of primer hybridization, extending and denaturing steps to provide an intermediate double stranded DNA molecule containing a promoter sequence through the use of a promoter sequence-containing primer. The double stranded DNA is used to produce multiple RNA copies of the target sequence. The resulting RNA copies can be used as target sequences to produce further copies, and multiple cycles can be performed. (See, e.g., Burg, et al., WO 89/1050; Gingeras, et al., WO 88/10315 (sometimes called "transcription amplification system" or TAS); EPO Application No. 89313154 to Kacian and Fultz; EPO Application No. 88113948.9 to Davey and Malek; Malek, et al. WO91/02818.)

Walker, et al., Proc. Natl. Acad. Sci. (USA) 89:392–396 (Jan. 1992), not admitted to be prior art, describes an oligonucleotide driven amplification method for use with a DNA template, using a restriction endonuclease to produce the initial target sequences and an enzyme to nick the DNA/DNA complex in order to enable an extension reaction and therefore amplification. Becker, et al., EPO Application No. 88306717.5, describes an amplification method in which a primer is hybridized to the target sequence and the resulting duplex is cleaved prior to the extension reaction and amplification; in the case where the primer extends past the region of hybridization, it requires cleavage prior to the extension and the primer must be blocked at its 3'-end to prevent any unwanted extension reactions from occurring prior to amplification. Urdea, WO 91/10746, describes a signal amplification method that incorporates a T7 promoter sequence.

Other methods of amplifying nucleic acid include the ligase chain reaction (LCR), described in European Patent Application No. 320,308, in which at least four separate oligoprobes are used; two of the oligoprobes hybridize to opposite ends of the same target strand in appropriate orientation such that the third and fourth oligoprobes may hybridize with the first and second oligoprobes to form, upon ligation, connected probes that can be denatured and detected. Another method is that described in EPO Application No. 0 427 073 A2, published May 15, 1991 and not admitted to be prior art, in which a palindromic probe able to form a hairpin and having a functional promoter region in the hairpin is hybridized to a target sequence, then ligated to another oligonucleotide hybridized to the target sequence such that specific RNA transcripts may be made.

Relatively large amounts of certain RNAs may be made using a recombinant single-stranded RNA molecule having a recognition sequence for the binding of an RNA-directed polymerase, preferably Qβ replicase. (See, e.g., U.S. Pat. No. 4,786,600 to Kramer, et al.) A number of steps are required to insert the specific sequence into a DNA copy of the variant molecule, clone it into an expression vector, transcribe it into RNA and then replicate it with Qβ replicase.

Definitions

As used herein, the following terms have the following meanings unless expressly indicated to the contrary.

A. Nucleic Acid

"Nucleic acid" means either RNA or DNA, along with any nucleotide analogues or other molecules that may be present in the sequence and that do not prevent performance of the present invention.

B. Template

A "template" is a nucleic acid molecule that is able to be copied by a nucleic acid polymerase. A template may be either RNA or DNA, and may be any of single-stranded, double-stranded or partially double-stranded, depending on the polymerase. The synthesized copy is complementary to the template. In this invention, the term copies also includes nucleic acid having the equivalent RNA or DNA sequence to a template, which are commonly referred to as homologous sequences in the art.

C. Primer

A "primer" is an oligonucleotide that is complementary to a template that hybridizes with the template to give a primer/template complex for initiation of synthesis by a DNA polymerase, such as a reverse transcriptase, and which is extended by the addition of covalently bonded bases linked to its 3' end that are complementary to the template. The result is a primer extension product. Virtually all DNA polymerases (including reverse transcriptases) that are known require complexing of an oligonucleotide to a single-stranded template ("priming") to initiate DNA synthesis. Under appropriate circumstances, a primer may be a part of a promoter-primer. Such primers are generally between 10 and 100 bases in length, preferably between 20 and 50 bases in length.

D. Promoter or Promoter Sequence

A "promoter" or "promoter sequence" is a specific nucleic acid sequence that is recognized by a DNA-dependent RNA polymerase ("transcriptase") as a signal to bind to a nucleic acid molecule and begin the transcription of RNA at a specific site. For binding, such transcriptases generally require that the promoter and its complement be double-stranded; the template portion need not be double-stranded. Individual DNA-dependent RNA polymerases recognize a variety of different promoter sequences that can vary markedly in their efficiency of promoting transcription. When an RNA polymerase binds to a promoter sequence to initiate transcription, that promoter sequence is not part of the sequence transcribed. Thus, the RNA transcripts produced thereby will not include the promoter sequence.

E. Promoter-primer

A promoter-primer comprises a promoter and a primer. It is an oligonucleotide that is sufficiently complementary to the 3'-end of a target nucleic acid sequence to complex at or near the 3'-end of that target nucleic acid sequence, which means that the promoter-primer complexes near enough the end of the target sequence to allow amplification of enough of the target sequence that the requirements of the assay, testing, cloning or other use for the amplified nucleic acid are met. The promoter-primer is used as a template to create a complementary nucleic acid sequence extending from the 3'-end (also known as the 3' terminus) of a target nucleic acid sequence, to result in a generally double stranded promoter, subject to any denaturing or enzymatic activity that may disrupt the double strand. Such promoter-primers are generally between 40 and 100 bases in length, preferably between 40 and 60 bases.

A DNA- or RNA-dependent DNA polymerase also creates a complementary strand to the target nucleic acid molecule, using the target sequence as a template.

F. Modified Primer or Promoter-primer

The 3'-end of the primer or promoter-primer may be modified, or blocked, so as to prevent or reduce the rate and/or extent of an extension reaction from proceeding therefrom. A primer or promoter-primer having both modified and unmodified members consists of essentially the same nucleic acid sequence for the purposes of the present invention. In other words, the modified primer or promoter-primer does not contain a different complexing sequence (primer) in that both the modified and unmodified oligonucleotide hybridize in effectively the same position (plus or minus about ten bases) on the target nucleic acid sequence. Also, the modified promoter-primer does not contain a different recognition sequence (promoter) from the unmodified promoter-primer. This means that, within about 10 bases, the modified and unmodified primers or promoter-primers are the same, are recognized by the same RNA polymerase, and hybridize to more or less the same target sequence (although not necessarily at precisely the same position). In a preferred embodiment, the modified and unmodified primers or promoter-primers are identical except for the modification.

The 3'-end of the target complementary portion of a primer or promoter-primer can be modified in a variety of ways well known to those skilled in the art. Appropriate modifications to a promoter-primer can include addition of ribonucleotides, 3' deoxynucleotide residues, (e.g., cordycepin (CO, Glen Research)), 3',2'-dideoxy nucleotide residues, modified nucleotides with nonphosphodiester backbone linkages (such as phosphorothioates), and non-nucleotide linkages such as described in Arnold, et al., (PCT US 88/03173) (RS) or alkane-diol modifications (Wilk et al. Nuc. Acids Res. 18:2065, 1990) (RP), or the modification may simply consist of one or more nucleotide residues 3' to the hybridizing sequence that are uncomplementary to the target nucleic acid. Of course, other effective modifications are possible as well.

A mixture of modified and unmodified oligonucleotides may be used in an amplification reaction, and a broad range of ratios of modified to unmodified oligonucleotide (e.g., from 1:1 to 1,000:1) can be used. A mixture of oligonucleotides with different 3' modifications may also be used.

G. Plus (+) and Minus (−) Strand(s)

Discussions of nucleic acid synthesis are greatly simplified and clarified by adopting terms to name the two complementary strands of a nucleic acid duplex. Traditionally, the strand encoding the sequences used to produce proteins or structural RNAs was designated as the "plus" strand and its complement the "minus" strand. It is now known that in many cases, both strands are functional, and the assignment of the designation "plus" to one and "minus" to the other must then be arbitrary. Nevertheless, the terms are very useful for designating the sequence orientation of nucleic acids and will be employed herein for that purpose, with the "plus" strand denominating the original target sequence strand that is complexed with the first primer or promoter-primer.

H. Target Nucleic Acid Sequence, Target Sequence

A "target nucleic acid sequence," or "target sequence," has a desired nucleic acid sequence to be amplified, and may be either single-stranded or double-stranded and may include other sequences 5' or 3' of the sequences to be amplified which may or may not be amplified.

The target nucleic acid sequence includes the complexing sequences to which the promoter-primer hybridizes during performance of the present invention. Where the target nucleic acid sequence is originally single-stranded, the term refers to either the (+) or (−) strand, and will also refer to the sequence complementary to the target sequence. Where the target nucleic acid sequence is originally double-stranded, the term refers to both the (+) and (−) strands.

I. DNA-Dependent DNA Polymerase

A "DNA-dependent DNA polymerase" is an enzyme that synthesizes a complementary DNA copy from a DNA template. An example is bacteriophage T7 DNA polymerase. All known DNA-dependent DNA polymerases require a complementary primer, which can be RNA or DNA, or a copolymer, to initiate synthesis. It is known that under suitable conditions certain DNA-dependent DNA polymerases may synthesize a complementary DNA copy from an RNA template.

J. DNA-Dependent RNA Polymerase (Transcriptase)

A "DNA-dependent RNA polymerase" or "transcriptase" is an enzyme that synthesizes multiple RNA copies from a double-stranded or partially-double stranded DNA molecule having a (usually double-stranded) promoter sequence. It should be noted that the present invention includes single stranded promoter sequences in the promoter-primer, along with the RNA polymerases that recognize them. The RNA molecules ("transcripts") are synthesized in the 5'→3' direction of the RNA molecule, beginning at a specific position just downstream of the promoter. Examples of transcriptases are the DNA-dependent RNA polymerases from bacteriophages T7, T3, and SP6.

K. RNA-Dependent DNA Polymerase (Reverse Transcriptase)

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with either the RNA or DNA templates.

L. RNAse H

An "RNAse H" is an enzyme that degrades the RNA portion of an RNA:DNA duplex. RNAse H's may be endonucleases or exonucleases. Avian myeloblastosis virus and Moloney murine leukemia virus reverse transcriptases contain an RNAse H activity in addition to their polymerase activity. Some cloned reverse transcriptases lack RNAse H activity. There are also sources of RNAse H available without an associated polymerase activity. The degradation may result in separation of RNA from an RNA:DNA complex. Alternatively, the RNAse H may simply cut the RNA at various locations such that portions of the RNA melt off or permit enzymes to unwind portions of the RNA, or the RNA fragments generated may serve as primers for extension by a polymerase.

M. Hybridize, Complex

The terms "hybridize" and "complex" refer to the formation of duplexes between nucleotide sequences that are sufficiently complementary to form duplexes (or "complexes") via Watson-Crick base pairing. Where a promoter-primer or primer "hybridizes" with target (template), such complexes (or hybrids) are sufficiently stable to serve the priming function required by a DNA polymerase to initiate DNA synthesis.

N. Specificity

Specificity is a characteristic of a nucleic acid sequence that describes its ability to distinguish between target and non-target sequences, dependent on sequence and assay conditions.

SUMMARY OF THE INVENTION

The present invention is directed to a novel, autocatalytic method of synthesizing multiple copies of a target nucleic acid sequence (i.e., the method cycles automatically without the need to modify reaction conditions such as temperature, pH, or ionic strength).

The present invention features treating a target sequence with a first oligonucleotide (that has a complexing sequence sufficiently complementary to a 3'-end portion of the target sequence to hybridize therewith (this alone is termed a primer), and that has a sequence 5' to the complexing sequence that includes a sequence which, in double-stranded form, acts as a promoter for an RNA polymerase (this arrangement is termed a promoter-primer)), and a second oligonucleotide (which is a primer or promoter-primer that has a complexing sequence sufficiently complementary to the complement of the target sequence to hybridize therewith), under conditions in which an oligonucleotide/target sequence complex may be formed and DNA and RNA synthesis may occur. In this invention, one or both of the first and second oligonucleotides is a mixture of a blocked and an unblocked oligonucleotide sequence (blocked oligonucleotides have a modified 3' end to prevent or reduce the rate and/or extent of primer extension by a DNA polymerase), or a mixture of oligonucleotides with different 3' modifications. Such a mixture significantly enhances the efficiency of the specific amplification reaction compared to use of only blocked or only unblocked oligonucleotides. The ratio of such oligonucleotides can be varied dependent upon the specific template sequence to be amplified, but generally is between 1:1 and 1000:1 blocked to unblocked. The invention does not require that the target sequence have defined 3'- or 5'-ends.

One aspect of the invention includes (a) treating a target sequence with a first promoter-primer oligonucleotide that has a complexing sequence sufficiently complementary to a 3'-end portion of the target sequence to hybridize therewith, and that has a sequence 5' to the complexing sequence that includes a sequence which, in double-stranded form, acts as a promoter for an RNA polymerase, under conditions in which an oligonucleotide/target sequence complex may be formed and DNA synthesis may be initiated by an appropriate polymerase (e.g., a DNA polymerase), (b) incubating the first oligonucleotide/target complex under extension reaction conditions so that the 3'-end of the target may be extended to produce a hybrid template for an RNA polymerase; and (c) incubating the hybrid template under conditions in which multiple RNA copies of the target sequence may be produced using an RNA polymerase that recognizes the promoter sequence. The invention also includes generation of a 3'-end of an RNA target sequence in step (b) by the action of an enzyme that selectively degrades the RNA portion of an RNA:DNA hybrid (e.g., RNase H). The RNA so produced may autocatalytically cycle to produce more product.

In other methods, the invention features (a) contacting a nucleic acid (e.g., RNA or DNA) target sequence with a first oligonucleotide primer or promoter-primer under conditions in which a first oligonucleotide/target sequence complex is formed such that DNA synthesis may be initiated by an appropriate polymerase (e.g., a DNA polymerase), (b) incubating the first oligonucleotide under extension reaction conditions so that the target may be used by the polymerase as a template to give a first DNA extension product complementary to the target (if the first primer is not blocked); (c) if the target is an RNA molecule, separating the DNA extension product from the RNA target using an enzyme that selectively degrades the RNA target, or if the target is a DNA molecule, separating the two DNA strands (e.g., by heating at 90°–100° C., or by other means); (d) contacting the DNA extension product with a second oligonucleotide that includes a primer or a promoter-primer, and that has a complexing sequence sufficiently complementary to the 3'-end portion of the DNA extension product to hybridize therewith under conditions in which a second oligonucleotide/extension product complex is formed and DNA synthesis may be initiated as above, depending on any blocking molecules on this primer. In this invention, if the first oligonucleotide is not a promoter-primer, then the second oligonucleotide is a promoter-primer, which means the second oligonucleotide has a sequence 5' to the complexing sequence that includes a promoter sequence for an RNA polymerase. In addition, the first and/or second oligonucleotides consist of either a mixture of a blocked and an unblocked oligonucleotide, or a mixture of oligonucleotides with different 3' modifications.

The amplification reaction is performed in a mixture consisting essentially of the necessary reactants and reagents. However, such a mixture may also contain enzymes or other substituents that do not qualitatively affect the amplification of the invention (e.g., the mechanism of the reaction). Such substituents may affect the amount of amplification observed. For example, the mixture may contain other promoter-primers for the same target sequence, or may contain "helper" oligonucleotides. Such helper oligonucleotides are used in a manner similar to the hybridization helper probes described by Hogan et al., U.S. Pat. No. 5,030,557 (hereby incorporated by reference herein), namely by aiding binding of the promoter-primer to its target nucleic acid, even if that target nucleic acid has significant secondary structure. Despite the similarity in use of such helper oligonucleotides, it was surprising that such helper oligonucleotides could be used in an amplification protocol without adverse effect on the efficiency of the procedure.

The first oligonucleotide may be a promoter-primer and the second oligonucleotide may be a primer, or vice versa, or both the first and second oligonucleotides may be promoter-primers, with either identical promoters (in the sense that the promoters are recognized by the same RNA polymerase) or different promoters. Use of different promoters is particularly useful when the amplified nucleic acid will be used for cloning. The first and second oligonucleotides and the RNA produced from the target sequence may then be used to autocatalytically synthesize multiple copies (by which is meant both complementary and homologous nucleic acid sequences) of the target sequence.

The modified primer or promoter-primer of the present invention consists essentially of a single nucleic acid sequence that has a modification at or near (within 3 bases) the 3'-end of the given primer or promoter-primer that alters (decreases or blocks) extension of the primer on a template by a DNA polymerase. Preferably this modified primer or promoter-primer is mixed with an unmodified primer or promoter-primer consisting essentially of the same nucleic acid sequence, along with one or more other primers or promoter-primers of a different nucleic acid sequence (that may also be a mixture of blocked and unblocked oligonucleotides). The invention also includes use of mixtures of primers and promoter-primers with more than one modification at or near their 3'-ends.

In addition, in another aspect of the present invention, where the sequence sought to be amplified is DNA, use of an appropriate preliminary procedure may enhance generation of RNA copies that may then be amplified according to the present invention. Accordingly, the present invention is also directed to preliminary procedures for use in conjunction with the amplification method of the present invention that not only can increase the number of copies to be amplified, but also can provide RNA copies of a DNA sequence for amplification.

In a further aspect, the invention features generation of a defined 5' end (i.e., one of known sequence) in an RNA target sequence by treating the RNA with a DNA oligonucleotide which hybridizes near the second primer binding site and thereby forms a substrate for RNAse H. This substrate is then cleaved by RNAse H to define the 5' end of the RNA target, which can be amplified as discussed above.

In another aspect, the present invention involves cooperative action of a DNA polymerase (such as a reverse transcriptase) and a DNA-dependent RNA polymerase (transcriptase) with an enzymatic hybrid-separation step to produce products that may themselves be used to produce additional product, thus resulting in an autocatalytic reaction without requiring manipulation of reaction conditions, such as in thermal cycling. Further, in some embodiments of the present invention that include a preliminary procedure, all but the initial step(s) of the preliminary procedure are carried out at one temperature.

The present invention may be used as a component of assays to detect and/or quantitate specific nucleic acid target sequences in clinical, environmental, forensic, and similar samples or to produce large numbers of copies of DNA and/or RNA of a specific target sequence for a variety of uses. These methods may also be used to produce multiple DNA copies of a DNA target for cloning, or to generate probes, or to produce RNA and DNA copies for sequencing.

In one example of a typical assay, a sample (including RNA or DNA target) to be amplified is mixed with a buffer concentrate containing the buffer, salts (e.g., divalent cations such as magnesium), nucleotide triphosphates, primers and/or promoter-primers (blocked and/or unblocked), a thiol reducing agent such as dithiothreitol, and a polycation such as spermidine. The reaction is then optionally incubated near 100° C. to denature any secondary structure. After cooling to room temperature (about 20° C.), enzymes containing DNA and RNA dependent DNA polymerase activity, RNAse H activity and DNA dependent RNA polymerase activity are added and the mixture is incubated for about 10 minutes to four hours at 37° C. to 42° C. The reaction can then be assayed by adding a luminescently-labelled probe, incubating 10 to 30 minutes at 60° C., adding a solution to selectively hydrolyze the label on unhybridized probe, incubating the reaction for 5 to 10 minutes at 60° C., and measuring the remaining chemiluminescence in a luminometer. (See, e.g., Arnold, et al., PCT US88/02746 (filed Sep. 21, 1988, published Mar. 29, 1989) the disclosure of which is incorporated herein by reference and is referred to as "HPA".) The products of the invention may be used in many other assay systems known to those skilled in the art.

Optionally, a DNA target without a defined 3'-end, can be incubated near 100° C. to denature any secondary structure and cooled to room temperature. Reverse transcriptase is added and the reaction mixture is incubated for 12 minutes at 42° C. The reaction is again denatured near 100° C., this time to separate the primer extension product from the DNA template. After cooling, enzymes with DNA and RNA dependent DNA polymerase activity, RNAse H activity and DNA dependent RNA polymerase are added and the reaction is incubated for 10 minutes to four hours at 37° C.–42° C. For a DNA target, a defined 3'-end can be created by use of a restriction endonuclease. A defined 3'-end may also be generated by other means known in the art.

Yet another aspect of the invention features a composition consisting essentially of a first and a second oligonucleotide of opposite sense and able to hybridize at or near the 3'-end of a target nucleic acid sequence and its complement, respectively, wherein one of the oligonucleotides is a promoter-primer and the other may be either a primer or a promoter-primer, and one or both of the oligonucleotides consists essentially of a mixture of a single nucleic acid sequence having either a modified or an unmodified 3'-end, a DNA-dependent DNA polymerase, an RNA-dependent DNA polymerase, and an RNA polymerase, wherein the mixture allows amplification at effectively constant pH, concentration and temperature (i.e., none of the recited conditions need be actively changed by the user). The composition may also include an RNAse H activity and/or other components described herein.

In other aspects, the invention features kits containing oligonucleotides including specific sequences useful in this amplification method, or in other amplification methods, such as those described above. Such sequences include those listed in the SEQUENCE LISTING, and may be attached to other sequences recognized by an enzyme (such as a polymerase, or restriction endonuclease). In particular, these oligonucleotides are useful for amplifying Mycobacterium nucleic acid, e.g., that of *M. tuberculosis*, and may have modified 3'-ends as discussed above.

The materials used in the present invention may be incorporated as part of diagnostic kits or other kits for use in diagnostic procedures, or other procedures, and the invention is adaptable to multi-well technology which may be provided in kit format.

DETAILED DESCRIPTION OF THE INVENTION

Figure 1:
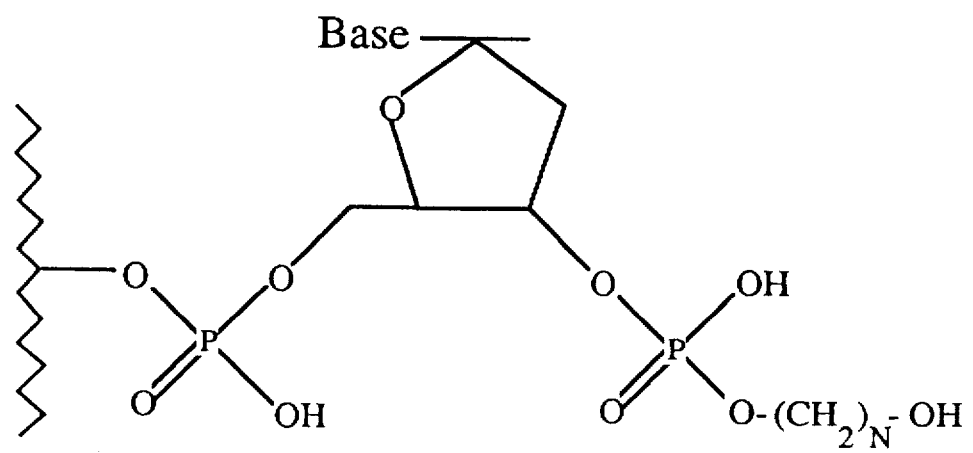
FIG. 1 shows the structure of the alkane-diol modification referred to as RP.

In accordance with the present invention, a novel method, composition and kit are provided for the amplification of specific nucleic acid target sequences for use in assays for the detection and/or quantitation of specific nucleic acid target sequences or for the production of large numbers of copies of DNA and/or RNA of specific target sequences for a variety of uses.

The present invention advantageously provides an amplification method that synthesizes RNA copies of a target sequence by use of a mixture of blocked and unblocked promoter-primers, or promoter-primers with different 3' modifications, consisting essentially of the same nucleic acid sequence in a ratio that provides for lessened non-specific byproducts. In the present invention, the amplification process occurs spontaneously and isothermally under a broad range of conditions. The amplification reactions described below are a series of logical steps. The relative rate of each step will determine the effective yield of amplification product. Use of a mixture of blocked and unblocked primers reduces the side reactions, and hence improves amplification. Side products, such as "primer-dimers" have been described, and are well known in the art to affect the efficiency of amplification reactions. The present invention reduces the efficiency of formation of such byproducts, therefore enhancing amplification efficiency.

Suitable DNA polymerases for the present invention include reverse transcriptases such as avian myeloblastosis virus (AMV) reverse transcriptase and Moloney murine leukemia virus (MMLV) reverse transcriptase. Promoters or promoter sequences suitable for incorporation in promoter-primers used in the present invention are nucleic acid sequences (either naturally occurring, produced synthetically or by a restriction endonuclease digest) that are specifically recognized by an RNA polymerase that recognizes and binds to that sequence and initiates the process of transcription whereby RNA transcripts are produced. Promoter sequences for which there is a known and available polymerase that is capable of recognizing the initiation sequence are particularly suitable to be employed. Such promoters include those that are recognized by certain bacteriophage polymerases such as those from bacteriophage T3, T7 or SP6. The sequence may optionally include nucleotide bases extending beyond the actual recognition site for the RNA polymerase that may impart added stability or susceptibility to degradation processes or increased transcription efficiency.

Although some of the reverse transcriptases suitable for use in the present invention have an RNAse H activity, such as AMV or MMLV reverse transcriptase, it may be preferred to add exogenous RNAse H, such as E. coli RNAse H. For example, although the Examples (see below) show that the addition of exogenous RNAse H is not required, the RNAse H activity present in AMV reverse transcriptase may be inhibited by relatively large amounts of heterologous DNA present in the reaction mixture; one solution to the problem is to add exogenous RNAse H. Another instance when added RNAse H may be required is when an oligonucleotide hybridizes internally (i.e., the oligonucleotide hybridizes such that target sequence nucleotides extend past both the 3' and 5' ends of the oligonucleotide) on the target RNA.

The present invention does not require a denaturation step to separate the RNA-DNA complex produced by the first DNA extension reaction. Such denaturation steps require manipulation of reaction conditions such as by substantially increasing the temperature of the reaction mixture (generally from ambient temperature to about 80° C. to about 105° C.), reducing its ionic strength (generally by 10× or more) or changing pH (usually increasing pH to 10 or more). Such manipulations of the reaction conditions often deleteriously affect enzyme activities, requiring addition of additional enzyme and also necessitate further manipulations of the reaction mixture to return it to conditions suitable for further nucleic acid synthesis.

The second oligonucleotide in the mixture may be blocked or modified similarly to the first oligonucleotide. In one aspect of the present invention, if the first oligonucleotide is unmodified, then the second oligonucleotide is modified. Also, if the first oligonucleotide is not a promoter-primer, then the second oligonucleotide is a promoter-primer. Further, if the first oligonucleotide is only a primer, then it may be unblocked, and the second oligonucleotide is then a promoter-primer including both blocked and unblocked constituents consisting essentially of a single nucleic acid sequence.

Surprisingly, such a mixture of blocked and unblocked oligonucleotides consisting essentially of the same nucleic acid sequence reduces the amount of non-specific product formation, and thereby increases the effectiveness of the amplification.

The RNA copies or transcripts produced may autocatalytically multiply without further manipulation.

In another aspect of the present invention, the first and second oligonucleotides are both promoter-primers, and either or both may each consist of both modified and unmodified promoter-primers. In such a case, it is preferred that both promoters are recognized by the same RNA polymerase unless it is intended to introduce the second promoter for purposes other than amplification, such as cloning. Where both oligonucleotides are promoter-primers, then transcripts complementary to both strands of the double-stranded template will be produced during the autocatalytic reaction and the number of copies of the target sequence synthesized may be enhanced.

Note that, as the first oligonucleotide (primer or promoter-primer) defines one end of the target sequence, the second oligonucleotide (primer or promoter-primer) now defines the other end; the termini may also be defined by a specific restriction endonuclease, or by other suitable means (which may include a natural 3'-end). The RNA transcripts may have different termini from the original target nucleic acid, but the sequence between the first oligonucleotide and the second oligonucleotide remains intact. The RNA transcripts so produced may automatically recycle in the above system without further manipulation. Thus, this reaction is autocatalytic.

Also note that either oligonucleotide may have nucleotide sequences 5' to its priming sequence that can result in the addition of extra nucleotide sequence to the eventually resulting double stranded DNA; the extra nucleotide sequence is not limited to a promoter sequence.

In another embodiment, the present invention may consist of a first and second oligonucleotide in which a promoter-primer is provided which consists only of a blocked oligonucleotide, or only of an unblocked oligonucleotide, or an oligonucleotide with a mixture of different modifications at or near the 3'-end.

In further embodiments, the amplification is performed in the presence of additives to enhance amplification. Examples such as dimethyl sulfoxide, dimethyl formamide, ethylene glycol, glycerol or zinc have been used.

The components of the reaction mixture may be added stepwise or at once. The reaction advantageously takes place under conditions suitable for maintaining the stability of reaction components, such as the component enzymes, and without requiring modification or manipulation of reaction conditions during the course of the amplification reaction.

The present invention may be used as a component of assays to detect and/or quantitate specific nucleic acid target sequences in clinical, environmental, forensic, and similar samples or to produce large number of copies of DNA and/or RNA of specific target sequence for a variety of uses.

EXAMPLES

Preface

The following examples demonstrate the utility of the methods of the present invention. They are not limiting and should not be considered as such.

Unless otherwise specified the reaction conditions for amplification used in the following examples were 50 mM Tris-HCl, 35 mM KCl, 20 mM $MgCl_2$, 15 mM N-acetylcysteine, 4 mM rATP, 4 mM rCTP, 4 mM rGTP, 4 mM rUTP, 1 mM dATP, 1 mM dCTP, 1 mM dGTP, 1 mM dTTP, 10% glycerol, 10% dimethyl sulfoxide, 300–600 units MMLV reverse transcriptase, 200–400 units T7 RNA polymerase, 0.15 µM each primer or promoter-primer, and specified amounts of template and enzymes in 100 µl volumes at 42° C. for one hour. Dithiothreitol, spermidine and/or polyethyleneimine (PEI) may also advantageously be added to the reaction mixture.

The enzymes used in the following examples are T7 or T3 RNA polymerase and Moloney murine leukemia virus (MMLV) reverse transcriptase. Other RNA polymerases with different promoter specificities are also suitable.

The relative amplification was measured as follows. A sample of the amplification reaction mixture (usually 10 µl) was added to 100 µl of a luminescently labelled probe (for example, labelled with an acridinium ester—see HPA reference above) solution containing approximately 75 fmol probe, 0.1 M lithium succinate, pH 4.7, 2% (w/v) lithium lauryl sulfate, 15 mM aldrithiol, 20 mM EDTA, and 20 mM EGTA, and mixed. The reactions were then incubated 20 minutes at 60° C. and cooled. To each hybridization reaction was added 300 µl of 0.6 M sodium borate pH 8.5, 1% Triton X-100. The reactions were then mixed and incubated six minutes at 60° C. to destroy the chemiluminescent label of the unhybridized probe. This method of destruction of the chemiluminescent label of unhybridized probe is quite specific; only a very small fraction of the unhybridized probe remains chemiluminescent. The reactions were cooled and the remaining chemiluminescence was quantified in a luminometer upon the addition of 200 µl 0.1% hydrogen peroxide. 1 mM nitric acid, and surfactant, and 200 µl 1.0 N sodium hydroxide. In the assay, hybridized probe emits light. The quantity of photons emitted are measured in a luminometer and the results are reported as Relative Light Units or RLU. Since the reaction that destroys the chemiluminescent label of unhybridized probe is not 100% effective, there is generally a background level of signal present in the range of about 1000 to 2000 RLU.

Many other assay methods are also applicable, including assays employing hybridization to isotopically labeled probes, blotting techniques and electrophoresis.

These reaction conditions are not necessarily optimized, and have been changed as noted for some systems. The oligonucleotide sequences used are exemplary and are not meant to be limiting as other sequences have been employed for these and other target sequences.

Example 1

To show that amplification occurred with a modified promoter-primer complementary to a sequence within an RNA target, a promoter-primer complementary to a sequence within *M. tuberculosis* rRNA (Seq ID No. 1) was synthesized either unmodified or with a 3' alkane diol (RP) or 3' cordycepin (CO) and incubated with a primer of the same sense as the target RNA (Seq ID No. 2) and 3 tmol ($10^{-21}$ mol) of target under the conditions described above. The reactions were analyzed with a probe of the same sense as the target RNA (Seq ID No. 3) with helper oligonucleotides as described in Hogan (U.S. Pat. No. 5,030,557, Means for Enhancing Nucleic Acid Hybridization, Seq ID Nos. 4 and 5). The results show that significant amplification does occur with a promoter-primer containing a 3' modification.

| Promoter-primer modification | RLU |
|---|---|
| Unmodified | 314,445 |
| 3'cordycepin | 71,382 |
| Unmodified | 683,737 |
| 3'-RP | 70,014 |

Example 2

In this experiment, a promoter-primer with a sequence complementary to *M. tuberculosis* 23S rRNA was modified by the presence of a 3' phosphorothioate nucleotide. Fifteen pmol of promoter-primer and primer (Seq ID Nos. 6 and 7) were used to amplify 0.3 tmol of target RNA, followed by detection with probe the same sense as the target RNA (Seq ID No. 8) with helper probes (Seq. ID Nos. 9 and 10). The results show that 3' phosphorothioate modified promoter-primer worked as well as unmodified oligonucleotide.

| Promoter-primer | RLU + target | RLU − target |
|---|---|---|
| Unmodified | 2,614,079 | 899 |
| 3' phosphorothioate | 2,570,798 | 647 |

Example 3

To show that mixtures of modified and unmodified promoter-primers function in an amplification assay, reactions were performed with 15 pmol of the primer and a promoter-primer (see below) and assayed as described in Example 1. Three tmol of target RNA was used.

| | | Pmol Promoter-primer | | |
|---|---|---|---|---|
| | | Unmodified | CO-modified | RLU |
| Experiment 1 | +Target | 15 | 0 | 834,902 |
| | +Target | 3 | 12 | 971,938 |
| | −Target | 3 | 12 | 1,456 |
| Experiment 2 | +Target | 3 | 12 | 1,015,199 |
| | +Target | 0.1 | 15 | 961,041 |

The results show that a mixture of blocked and unblocked oligonucleotides worked as well or better than all unblocked even at a ratio of 1:150 unblocked to blocked.

Example 4

In this experiment 3 tmol of target RNA were incubated with different concentrations of CO blocked and unblocked primer and a mixture of 15 pmol CO blocked promoter-primer and 0.1 pmol unblocked promoter-primer as in Example 1. Products were detected by hybridization assay.

| Pmol Primer | | |
|---|---|---|
| Blocked | Unblocked | RLU |
| 0 | 15 | 969,522 |
| 10 | 5 | 802,840 |
| 13 | 2 | 648,271 |

In addition to the satisfactory amplification observed, it was surprisingly found that the amount of non-template directed product was significantly less in the reactions performed with blocked oligonucleotides compared to reactions performed with unblocked oligonucleotides.

Example 5

In this experiment, the effect of mixing a single oligonucleotide sequence with two different 3' modifications was demonstrated. Three tmol of target RNA was amplified as in Example 1. The promoter-primer was synthesized with an unblocked 3'-end, blocked with RP, or CO blocked. Two pmol of primer were used.

| Pmol Promoter-primer | | | |
|---|---|---|---|
| RP modified | CO modified | Unmodified | RLU |
| 0 | 15 | 0.1 | 450,157 |
| 2 | 13 | 0.01 | 681,647 |
| 2 | 13 | 0 | 678,871 |
| 5 | 10 | 0 | 755,839 |

This example shows that a mixture of unmodified and modified or a mixture of different types of modified promoter-primers amplified well, allowing detection of 3 tmol of RNA target in one hour.

Example 6

In this example, a mixture of modified and unmodified primers and promoter-primers were used to amplify 3 tmol *M. tuberculosis* rRNA. A mixture of 2 pmol RP-modified promoter-primer and 13 pmol of CO-modified promoter-primer were incubated with unmodified primer or a mixture of unmodified primer and primer synthesized with a 3' phosphorothioate nucleotide (PS). The sequences and hybridization probes are as in Example 1.

| Primer modification | | |
|---|---|---|
| Unmodified | PS modified | RLU |
| — | 15 pmol | 118,411 |
| 1 pmol | 14 pmol | 364,733 |
| No target | | 1,266 |

Under these conditions, the mixture of modified and unmodified primers work best.

Example 7

In this example, 80 tmol of *Neisseria gonorrhoeae* rRNA was amplified with a primer complementary to the rRNA (Seq. I.D. No. 13) and a mixture of 28 pmol 3'-RP blocked- and 2 pmol unblocked promoter primer of the same sense as the RNA target (Seq. I.D. No. 14). In some reactions, a 3'-blocked oligonucleotide (Seq. I.D. No. 15) capable of hybridizing to *N. gonorrhoeae* rRNA and forming an RNAse H substrate, was added to the amplification. An aliquot of the reactions was hybridized to an AE-labeled probe and two helper probes complementary to the rRNA sequence (Seq. I.D. Nos. 16, 17, and 18, respectively).

RLU—RNAse H substrate oligo RLU+RNAse H substrate oligo

| RLU − RNAse H substrate oligo | RLU + RNAse H substrate oligo |
|---|---|
| 7,910 | 32,473 |
| 16,337 | 728,246 |
| 17,304 | 80,487 |
| 12,518 | 51,893 |

Example 8

In this example, 3 or 30 tmol of *M. tuberculosis* rRNA was amplified with a primer (Seq. I.D. No. 7) and a mixture of 14 pmole of 3'-RP blocked- and 1 pmol unblocked promoter primer containing a promoter for T3 RNA polymerase (Seq. I.D. No. 19). The reaction was performed as in Example 1 except that 450 units of MMLV RT were used, 200 units of T3 RNA polymerase replaced the T7 RNA polymerase, and the reaction was terminated after 40 minutes.

| Target concentration | RLU value |
|---|---|
| 30 tmol | 358,053 |
| 3 tmol | 75,440 |
| 0 tmol | 553 |

The results demonstrate that a mixture of blocked and unblocked promoter primer can be used to amplify RNA using reverse transcriptase and T3 RNA polymerase.

Example 9

In this example, amplification of a DNA target with an RP modified promoter primer was examined. Three tmol of cloned HIV-1 DNA was incubated with 30 pmol of a primer with sequence 5'-ATAATCCACCTATCCCAGTA GGAGAAAT-3' (SEQ. ID. NO. 20) and a promoter primer with sequence 5'-AATTTAATACGACTCACTATA GGGAGACCACACCTTGTCTTATGTCCAGAATGCT-3' (SEQ. ID. NO. 21) at 95° C. for 5 minutes, then cooled to room temperature. After enzyme addition, the reaction was incubated at 37° C. for 2 hours. The conditions were 50 mM Tris-HCl, 40 mM potassium acetate pH 8, 18 mM MgCl$_2$, 5 mM DTT, 2 mM spermidine, 6.2 mM GTP, 6.2 mM ATP, 2 mM CTP, 2 mM UTP, 0.2 mM dTTP, 0.2 mM dATP, 0.2 mM dGTP, 0.2 mM dCTP, 800 U MMLV RT, 400 U T7 RNA polymerase. The promoter primer was unmodified or modified with an RP at the 3' end. The reactions were assayed with AE-labeled probe of the same sense as the primer. Results shown are the average of five replicates.

| Pmol promoter primer | | |
|---|---|---|
| Unmodified | Modified | Average RLU |
| 30 | 0 | 127,223 |
| 26 | 4 | 411,692 |
| 0 | 30 | 743,877 |

It was unanticipated and surprising that amplification of a DNA target, especially one without a defined 3'-end, was not inhibited by the use of a modified promoter primer.

The present embodiments of this invention are to be considered in all respects as illustrative and not restrictive, the scope of the invention being indicated by the appended claims rather than by the foregoing description, and all changes which come within the meaning and range of equivalency of the claims therefore are intended to be embraced therein.

What is claimed is:

1. A method for producing multiple copies of a target nucleic acid comprising the steps of:
   a) incubating, under conditions in which an oligonucleotide/target sequence complex is formed and DNA and RNA synthesis occurs, a mixture comprising:
     a nucleic acid comprising a (+) target sequence,
     a first oligonucleotide comprising a primer sequence able to hybridize at or near the 3'-end of said (+) target sequence, a 5' promoter sequence, and a modification at or near the 3' end of said first oligonucleotide primer sequence which reduces or blocks extension of said first oligonucleotide primer sequence by a polymerase compared to said first oligonucleotide primer sequence not having said modification,
     a second oligonucleotide comprising a primer sequence able to hybridize at or near said 3'-end of said (+) target sequence, a 5' promoter sequence, and an optionally present modification at or near the 3' end of said second oligonucleotide primer sequence which reduces or blocks extension of said second oligonucleotide primer sequence by a polymerase compared to said second oligonucleotide primer sequence not having said modification, wherein said second oligonucleotide hybridizes to said (+) target sequence in effectively the same position as said first oligonucleotide and said second oligonucleotide modification, if present, is different than said first oligonucleotide modification,
     a third oligonucleotide comprising a primer sequence able to hybridize to the 3'-end of a (−) target nucleic acid sequence which is produced during said method and which is the complement of said (+) target sequence, an optionally present 5' promoter sequence, and an optionally present modification at or near the 3' end of said third oligonucleotide primer sequence able to reduce or block extension of said third oligonucleotide primer sequence by a polymerase compared to said third oligonucleotide primer sequence not having said modification,
     at least one enzyme activity selected from the group consisting of: DNA dependent DNA polymerase and RNA dependent DNA polymerase, and
     one or more RNA polymerases able to recognize said first and said second oligonucleotide 5' promoter sequences,
     wherein under said incubating conditions said third oligonucleotide facilitates production of said (+) target sequence using said (−) target sequence as a template, and
   b) producing said multiple copies of said target sequence.

2. The method of claim 1, wherein said method is performed without separating double-stranded nucleic acids by thermal cycling.

3. The method of claim 1, wherein said first and said second oligonucleotides hybridize within 10 bases of each other.

4. The method of claim 3, wherein said second oligonucleotide does not contain said modification.

5. The method of claim 4, wherein said first and said second oligonucleotides are present in a molar ratio of between 1:1 to 1000:1, respectively.

6. The method of claim 3, wherein said second oligonucleotide contains said modification.

7. The method of claim 6 further comprising the presence of a fourth oligonucleotide during said step (a), wherein said fourth oligonucleotide comprises a primer sequence able to hybridize in effectively the same position as said first and second oligonucleotides and an optionally present 5' promoter sequence, wherein said fourth oligonucleotide does not contain a modification at or near its 3' end able to reduce or block primer extension of said fourth oligonucleotide primer sequence compared to said fourth oligonucleotide primer sequence not having said modification.

8. The method of claim 6, wherein said first oligonucleotide modification and said second oligonucleotide modification are each independently selected from the group consisting of one or more: alkane diol modification, 3' deoxynucleotide residue, nucleotide with a nonphosphodiester linkage, non-nucleotide modification, base non-complementary to said (+) target sequence, and dideoxynucleotide.

9. The method of claim 6, wherein said first oligonucleotide modification and said second oligonucleotide modification are each independently selected from the group consisting of one or more: cordycepin, ribonucleotide, and phosphorothioate nucleotide.

10. The method of claim 3, wherein said third oligonucleotide does not contain said modification.

11. The method of claim 3, wherein said third oligonucleotide contains said 5' promoter sequence.

12. The method of claim 11, wherein said third oligonucleotide contains said modification.

13. The method of claim 12, further comprising a fourth oligonucleotide during said step (a), wherein said fourth oligonucleotide comprises a primer sequence able to hybridize to said (−) target sequence in effectively the same position as said third oligonucleotide, a 5' promoter sequence, and a modification at or near its 3' end able to reduce or block extension of said fourth oligonucleotide primer sequence by a polymerase compared to said fourth oligonucleotide primer sequence not having said modification, wherein said fourth oligonucleotide modification is different than said third oligonucleotide modification.

14. The method of claim 13, wherein said (+) target sequence is an RNA target sequence.

15. The method of claim 11, wherein said first oligonucleotide 5' promoter sequence, said second oligonucleotide 5' promoter sequence and said third oligonucleotide 5' promoter sequence are the same.

16. The method of claim 11, wherein said first oligonucleotide 5' promoter sequence is the same as said second oligonucleotide 5' promoter sequence, and said first and second 5' promoter sequences are different from said third oligonucleotide 5' promoter sequence.

17. The method of claim 3, wherein said first and said second oligonucleotide primer sequences are the same.

18. The method of claim 3, wherein said first and said second oligonucleotide primer sequences are different.

19. The method of claim 3, wherein said (+) target sequence is an RNA target sequence.

20. The method of claim 3, wherein said step (a) further comprises the presence of an RNAse H activity.

21. The method of claim 20, wherein said RNAse H activity is supplied by E. coli RNAse H.

22. The method of claim 20, wherein said RNAse H activity is supplied by a reverse transcriptase.

23. The method of claim 3, wherein said first oligonucleotide modification is selected from the group consisting of one or more: alkane diol modification, 3' deoxynucleotide residue, nucleotide with a nonphosphodiester linkage, non-nucleotide modification, base non-complementary to said (+) target sequence, and dideoxynucleotide.

24. The method of claim 3, wherein said first oligonucleotide modification is selected from the group consisting of one or more: cordycepin, ribonucleotide, and phosphorothioate nucleotide.

25. The method of claim 3 further comprising the step of detecting the presence or amount of nucleic acids produced by said step (b).

26. The method of claim 3 consisting essentially of said steps.

27. The method of claim 3, wherein said step (a) further comprises the presence of one or more agent selected from the group consisting of: DMSO, dimethylformamide, ethylene glycol, glycerol, and zinc.

28. A method for producing multiple copies of a target nucleic acid sequence comprising the steps of:

a) incubating, under conditions in which an oligonucleotide/target sequence complex is formed and DNA and RNA synthesis occurs, a mixture comprising:

a nucleic acid comprising a (+) target sequence, a first oligonucleotide comprising a primer sequence able to hybridize to the 3'-end of said (+) target sequence, an optionally present 5' promoter sequence, and an optionally present modification at or near the 3' end of said first oligonucleotide primer sequence able to reduce or block extension of said first oligonucleotide primer sequence by a polymerase compared to said first oligonucleotide primer sequence not having said modification, a second oligonucleotide comprising a primer sequence able to hybridize at or near the 3'-end of a (−) target nucleic acid sequence which is produced during said method and which is the complement of said (+) target sequence, a 5' promoter sequence, and a modification at or near the 3' end of said second oligonucleotide primer sequence which reduces or blocks extension of said second oligonucleotide primer sequence by a polymerase compared to said second oligonucleotide primer sequence not having said modification, a third oligonucleotide comprising a primer sequence able to hybridize at or near said 3'-end of said (−) target sequence, a 5' promoter sequence, and an optionally present modification at or near the 3' end of said third oligonucleotide primer sequence which reduces or blocks extension of said third oligonucleotide primer sequence by a polymerase compared to said third oligonucleotide primer sequence not having said modification, wherein said third oligonucleotide hybridizes to said (−) target sequence in effectively the same position as said second oligonucleotide and said third oligonucleotide modification, if present, is different than said second oligonucleotide modification, at least one enzyme activity selected from the group consisting of: DNA dependent DNA polymerase and RNA dependent DNA polymerase, and one or more RNA polymerases able to recognize said second and said third oligonucleotide 5' promoter sequences, wherein under said incubating conditions said first oligonucleotide facilitates production of said (+) target sequence using said (−) target sequence as a template, and b) producing said multiple copies of said target sequence.

29. The method of claim 28, wherein said method is performed without separating double-stranded nucleic acids by thermal cycling.

30. The method of claim 28, wherein said second and said third oligonucleotides hybridize within 10 bases of each other.

31. The method of claim 30, wherein said third oligonucleotide does not contain said modification.

32. The method of claim 31, wherein said second and said third oligonucleotides are present in a molar ratio of between 1:1 to 1000:1, respectively.

33. The method of claim 30, wherein said third oligonucleotide contains said modification.

34. The method of claim 33 further comprising the presence of a fourth oligonucleotide during said step (a), wherein said fourth oligonucleotide comprises a primer sequence able to hybridize in effectively the same position as said second and third oligonucleotides and an optionally present 5' promoter sequence, wherein said fourth oligonucleotide does not contain a modification at or near its 5' end able to reduce or block primer extension compared to said fourth oligonucleotide primer sequence not having said modification.

35. The method of claim 33, wherein said second oligonucleotide modification and said third oligonucleotide modification are each independently selected from the group consisting of one or more: alkane diol modification, 3' deoxynucleotide residue, nucleotide with a nonphosphodiester linkage, non-nucleotide modification, bases non-complementary to said (−) target sequence, and dideoxynucleotide.

36. The method of claim 33, wherein said second oligonucleotide modification and said third oligonucleotide modification each independently selected from the group consisting of one or more: cordycepin, ribonucleotide, and phosphorothioate nucleotide.

37. The method of claim 30, wherein said first oligonucleotide does not contain said modification.

38. The method of claim 30, wherein said first oligonucleotide contains said 5' promoter sequence.

39. The method of claim 38, wherein said first oligonucleotide contains said modification.

40. The method of claim 39 further comprising the presence of a fourth oligonucleotide during said step (a), wherein said fourth oligonucleotide comprises a primer sequence able to hybridize to said (+) target sequence in effectively the same position as said first oligonucleotide, a 5' promoter sequence, and a modification at or near its 3' end able to reduce or block extension of said fourth oligonucleotide primer sequence by a polymerase compared to said fourth oligonucleotide primer sequence not having said modification, wherein said fourth oligonucleotide modification is different than said first oligonucleotide modification.

41. The method of claim 40, wherein said (+) target sequence is an RNA target sequence.

42. The method of claim 38, wherein said first oligonucleotide 5' promoter sequence, said second oligonucleotide 5' promoter sequence, and said third oligonucleotide 5' promoter sequence are the same.

43. The method of claim 38, wherein said second oligonucleotide 5' promoter sequence is the same as said third oligonucleotide 5' promoter sequence, and second and said third 5' promoter sequences are different from said first oligonucleotide 5' promoter sequence.

44. The method of claim 30, wherein said second and said third oligonucleotide primer sequences are different.

45. The method of claim 30, wherein said (+) target sequence is an RNA target sequence.

46. The method of claim 30, wherein said step (a) further comprises the presence of an RNAse H activity.

47. The method of claim 46, wherein said RNAse H activity is supplied by *E. coli* RNAse H.

48. The method of claim 46, wherein said RNAse H activity is supplied by a reverse transcriptase.

49. The method of claim 30, wherein said second oligonucleotide modification is selected from the group consisting of one or more: alkane diol modification, 3' deoxynucleotide residue, nucleotide with a nonphosphodiester linkage, non-nucleotide modification, bases non-complementary to said (−) target sequence, and dideoxynucleotide.

50. The method of claim 30, wherein said second oligonucleotide modification is selected from the group consisting of one or more: cordycepin, ribonucleotide, and phosphorothioate nucleotide.

51. The method of claim 30 further comprising the step of detecting the presence or amount of nucleic acids produced by said step (b).

52. The method of claim 30 consisting essentially of said steps.

53. The method of claim 30, wherein said step (a) further comprises the presence of one or more agent selected from the group consisting of: DMSO, dimethylformamide, ethylene glycol, glycerol, and zinc.

* * * * *

UNITED STATES PATENT AND TRADEMARK OFFICE
CERTIFICATE OF CORRECTION

PATENT NO. : 5,766,849
DATED : June 16, 1998
INVENTOR(S) : Sherrol H. McDonough et al.

It is certified that error appears in the above-identified patent and that said Letters Patent is hereby corrected as shown below:

Column 26, Claim 28, Line 51: delete "(+)" and insert --(-)--

Column 26, Claim 28, Line 52: delete "(-)" and insert --(+)--

Column 27, Claim 34, Line 7: delete "5'" and insert --3'--

Signed and Sealed this

Eighth Day of June, 1999

Attest:

Q. TODD DICKINSON

Attesting Officer     Acting Commissioner of Patents and Trademarks

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
        ( A ) LENGTH: 62
        ( B ) TYPE: nucleic acid
        ( C ) STRANDEDNESS: single
        ( D ) TOPOLOGY: linear ( i i ) SEQUENCE DESCRIPTION: SEQ ID NO: 1:

GAAATTAATA CGACTCACTA TAGGGAGACC ACAGCCGTCA        40

GGGATAACCC CACCAACAAG CT                          62

( 2 ) INFORMATION FOR SEQ ID NO: 2:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 2:

GGGATAAGCC TGGGAAACTG GGTCTAATAC C                31

( 2 ) INFORMATION FOR SEQ ID NO: 3:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 3:

GTCTTGTGGT GGAAAGCGCT TTAG                        24

( 2 ) INFORMATION FOR SEQ ID NO: 4:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 4:

CCGGATAGGA CCACGGGATG CAT                         23

( 2 ) INFORMATION FOR SEQ ID NO: 5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION: SEQ ID NO: 5:

CGGTGTGGGA TGACCCCGCG                             20

( 2 ) INFORMATION FOR SEQ ID NO: 6:

( i ) SEQUENCE CHARACTERISTICS:
        ( A ) LENGTH: 47
        ( B ) TYPE: nucleic acid
        ( C ) STRANDEDNESS: single
        ( D ) TOPOLOGY: linear ( i i ) SEQUENCE DESCRIPTION: SEQ ID NO: 6:

AATTTAATAC GACTCACTAT AGGGAGACCA GGCCACTTCC       40

GCTAACC                                           47

( 2 ) INFORMATION FOR SEQ ID NO: 7:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 7:

CGCGGAACAG GCTAAACCGC ACGC                                                                  2 4

( 2 ) INFORMATION FOR SEQ ID NO: 8:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 8:

GGAGGATATG TCTCAGCGCT ACC                                                                   2 3

( 2 ) INFORMATION FOR SEQ ID NO: 9:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( i i ) SEQUENCE DESCRIPTION: SEQ ID NO: 9:

CGGCTGAGAG GCAGTACAGA AAGTGTCGTG GTTAGCGG                                                    3 8

( 2 ) INFORMATION FOR SEQ ID NO: 10:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) SEQUENCE DESCRIPTION: SEQ ID NO: 10:

GGGTAACCGG GTAGGGGTTG TGTGTGCGGG GTTGTG                                                      3 6

( 2 ) INFORMATION FOR SEQ ID NO: 11:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO: 11:

ATAATCCACC TATCCCAGTA GGAGAAAT                                                               2 8

( 2 ) INFORMATION FOR SEQ ID NO: 12:

( i ) SEQUENCE CHARACTERISTICS:
        ( A ) LENGTH: 55
        ( B ) TYPE: nucleic acid
        ( C ) STRANDEDNESS: single
        ( D ) TOPOLOGY: linear ( i i ) SEQUENCE DESCRIPTION: SEQ ID NO: 12:

AATTTAATAC GACTCACTAT AGGGAGACCA CACCTTGTCT                                                  4 0

TATGTCCAGA ATGCT                                                                             5 5

( 2 ) INFORMATION FOR SEQ ID NO: 13:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 13:

GCACGTAGTT AGCCGGTGCT TATTCTTCAG  30

( 2 ) INFORMATION FOR SEQ ID NO: 14:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( i i ) SEQUENCE DESCRIPTION: SEQ ID NO: 14:

AATTTAATAC GACTCACTAT AGGGAGAGCA AGCCTGATCC  40

AGCCATGCCG CGT  53

( 2 ) INFORMATION FOR SEQ ID NO: 15:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( i i ) SEQUENCE DESCRIPTION: SEQ ID NO: 15:

GCTTGCGCCC ATTGTCCAAA ATTTCCCACT GC  32

( 2 ) INFORMATION FOR SEQ ID NO: 16:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) SEQUENCE DESCRIPTION: SEQ ID NO: 16:

TCGGCCGCCG ATATTGGC  18

( 2 ) INFORMATION FOR SEQ ID NO: 17:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( i i ) SEQUENCE DESCRIPTION: SEQ ID NO: 17:

AACGGCCTTT TCTTCCCTGA CAAAAGTCCT TTACAACCCG  40

( 2 ) INFORMATION FOR SEQ ID NO: 18:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) SEQUENCE DESCRIPTION: SEQ ID NO: 18:

CGTAGTTAGC CGGTGCTTAT TCTTCAGGTA CCGTCA  36

( 2 ) INFORMATION FOR SEQ ID NO: 19:

( i ) SEQUENCE CHARACTERISTICS:
        ( A ) LENGTH: 46
        ( B ) TYPE: nucleic acid
        ( C ) STRANDEDNESS: single
        ( D ) TOPOLOGY: linear ( i i ) SEQUENCE DESCRIPTION: SEQ ID NO: 19:

TAATATTAAC CCTCACTAAA GGGAGACCAG GCCACTTCCG   40

CTAACC   46

( 2 ) INFORMATION FOR SEQ ID NO: 20:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO: 20:

ATAATCCACC TATCCCAGTA GGAGAAAT   28

( 2 ) INFORMATION FOR SEQ ID NO: 21:

( i ) SEQUENCE CHARACTERISTICS:
        ( A ) LENGTH: 55
        ( B ) TYPE: nucleic acid
        ( C ) STRANDEDNESS: single
        ( D ) TOPOLOGY: linear ( i i ) SEQUENCE DESCRIPTION: SEQ ID NO: 21:

AATTTAATAC GACTCACTAT AGGGAGACCA CACCTTGTCT   40

TATGTCCAGA ATGCT   55